United States Patent [19]

Nakamichi et al.

[11] Patent Number: 5,498,422
[45] Date of Patent: Mar. 12, 1996

[54] SUSTAINED RELEASE CAPSULE

[75] Inventors: Kouichi Nakamichi, Shiga; Shogo Izumi; Hiroshi Fukui, both of Kyoto, all of Japan

[73] Assignee: Nippon Shinyaku Company Limited, Japan

[21] Appl. No.: 129,187

[22] PCT Filed: Apr. 6, 1992

[86] PCT No.: PCT/JP92/00423

§ 371 Date: Oct. 7, 1993

§ 102(e) Date: Oct. 7, 1993

[87] PCT Pub. No.: WO92/17166

PCT Pub. Date: Oct. 15, 1993

[30] Foreign Application Priority Data

Apr. 8, 1991 [JP] Japan .................. 3-103846

[51] Int. Cl.⁶ .................................. A61K 9/52
[52] U.S. Cl. .............. 424/451; 424/452; 424/455; 424/457; 424/458; 514/772.6; 514/781; 514/964; 514/783
[58] Field of Search .................. 424/451, 457, 424/458, 452, 455

[56] References Cited

U.S. PATENT DOCUMENTS

| | | | |
|---|---|---|---|
| 4,002,731 | 1/1977 | Skulan | 424/494 |
| 4,250,163 | 2/1981 | Nagai et al. | 424/14 |
| 4,680,323 | 7/1987 | Lowey | 524/43 |
| 4,690,822 | 9/1987 | Uemura et al. | 424/455 |
| 5,064,650 | 11/1991 | Lew | 424/451 |

FOREIGN PATENT DOCUMENTS

| | | |
|---|---|---|
| 0107085 | 5/1984 | European Pat. Off. |
| 2555901 | 6/1985 | France |
| 3400106 | 7/1985 | Germany |
| 5441320 | 4/1979 | Japan |
| 1546448 | 3/1976 | United Kingdom |

Primary Examiner—Thurman K. Page
Assistant Examiner—James M. Spear
Attorney, Agent, or Firm—Roselman & Colin

[57] ABSTRACT

A sustained release capsule excellent in adhesion characteristics in the gastrointestinal tract, stability and so on is provided. The capsule is characterized in that a polymer excellent in initial adhesion and a polymer excellent in shape-retaining ability are dispersed in a liquid substance in the capsule, that a physiologically active substance is dispersed or dissolved in the liquid substance and that the moisture content in the whole preparation is not more than 2%.

22 Claims, 3 Drawing Sheets

△ : Example 1
● : Example 2
□ : Comparative Example 2

SUSTAINED RELEASE CAPSULE

TECHNICAL FIELD

The present invention relates to a capsule. More particularly, the invention relates to a sustained release capsule having good mucosa adhering property and stability.

BACKGROUND ART

Pharmaceutical preparations with which the drug concentration in blood can be maintained at a desired level for a prolonged period of time are very useful since the frequency of administration thereof can be reduced and the compliance can be improved. Such control of blood concentration can serve to avoid unnecessary increases in blood concentration and thereby reduce or alleviate adverse effects of the drug. Therefore, such pharmaceutical preparations are useful as compared with ordinary preparations.

Various dosage forms have been proposed as means of controlling the drug concentration in blood. For instance, there may be mentioned ① a preparation which comprises a core consisting of drug-containing granules and a semi-permeable coat film covering said core, so that the drug can be released therefrom gradually in a body fluid for prolongation of the drug action, ② gel matrix tablets that are made by admixing a water-soluble polymer having good gel forming ability with a drug and other appropriate ingredients and tableting the mixture for attaining sustained release by making use of the phenomenon of dissolution and peeling of the gel and ③ wax matrix tablets made by admixing a basically water-incompatible animal or vegetable oil or wax with a drug and tableting the mixture for attaining sustained release, among others.

However, the dosage forms mentioned above are invariably wanting in the function to control the transfer from the stomach to the small intestine after taking thereof and, as a result, cannot display satisfactory sustained release characteristics in many instances.

One of the means for solving this problem is to cause the pharmaceutical preparation to adhere to the gastrointestinal tract wall.

For instance, mention may be made of the method comprising coating pellets with an adhesive material (Japanese Kokai Tokkyo Koho JP 63-101332).

This technology comprises coating relatively large granular cores with an adhesive material to attain a sustained action. In this method, it is important that the adhesive material be used in large amounts to secure sustained release for a prolonged period of time.

However, to cover cores with a large amount of a highly sticky material is accompanied by problems very difficult to solve from the technology and cost viewpoints, for example measures for coping with secondary particles during handling and processing, and lowering the viscosity of the coating solution, which causes increases in process hours, for instance. In addition, since the adhesion time depends on the mutual relation between the adhesive power and detaching force (peeling force), such large grain size pellets show an adhesion time shortened due to the own weight of each grain as compared with fine particles.

Therefore, this technique is not always appropriate as a means of attaining sustained release by ensuring a long period of adhesion.

With another dosage form having adhesiveness, the transfer of a pharmaceutical preparation in the gastrointestinal tract is forcedly controlled by utilizing a carrier comprising a combination of an oil and a water-soluble polymer (Japanese Kokai Tokkyo Koho JP 61-233632).

Supposedly, this technique can prolong the adhesion time as compared with the method mentioned above because fine particles of a water-soluble polymer can be mixed in an oil.

However, it is evident that mere mixing of an oil with a water-soluble polymer does not necessarily give an excellent sustained release preparation. The reasons are as follows.

① When, for example, the affinity between the oil and water-soluble polymer is strong, the water-soluble polymer may be dissolved in the oil as the case may be. In that case, no adhesiveness is exhibited any longer.

② When the oil component is a liquid oil, the dosage form most preferred from the overall viewpoint, including administrability and economic aspects, will be a capsule form.

However, all oils are not utilizable in such a dosage form. For instance, propyleneglycol, glycerol, polyethylene glycol and the like, which are given as examples of the oil component in Japanese Kokai Tokkyo Koho JP 61-233632, when filled into hard capsules, will cause swelling, deformation or dissolution, for instance, of the capsule shell irrespective of the water-soluble polymer used combinedly.

Therefore, it is difficult to use such oil components as mentioned above in preparing carriers for sustained release for making encapsulated pharmaceutical preparations.

③ Furthermore, a polydiorganosiloxane is selected as the oil component in Japanese Kokai Tokkyo Koho JP 02-258718. However, said substance is physiologically active in that it can eliminate the gas in the gastrointestinal tract at a dose of about 120 mg per day. Naturally, it is not desirable to use such an oil component as an additive to pharmaceutical preparations.

On the other hand, the most serious problem raised by capsules filled with a dispersion composed of an oil and a water-soluble polymer is that when allowed to stand in an environment where the ambient air has a humidity of about 75%, the capsule contents tend to cake. A conceivable measure therefor may be strict moistureproof packaging for blocking the influence of moisture from outside. Even when such measure is taken, the phenomenon of caking still takes place. Thus, the contents, whether packed or not, will harden. This is a phenomenon specific to this dispersed system and is a physicochemical phenomenon not readily predictable in the current technology.

The caking phenomenon mentioned above involves not only physical changes of the contents but also loss of the adhesiveness of the carrier observable immediately after preparation thereof and, further, a rapid reduction in bioavailability, rendering the pharmaceutical preparation quite meaningless.

DISCLOSURE OF THE INVENTION

As mentioned above, it is evident that coating of pellets with an adhesive material or simple admixture of an arbitrarily selected oil with a water-soluble polymer, for instance, according to the prior art cannot satisfy basic important requirements for sustained release drug preparations, such as adhesiveness and stability. It is considered difficult to provide excellent sustained release preparations of the gastrointestinal tract adhering type without solving the problems mentioned above.

As a result of their intensive investigations made to solve the above problems, the present inventors found that a capsule which meets all the requirements ① to ⑦ mentioned below can be a sustained release preparation of the gastrointestinal tract adhesion type excellent in stability as a pharmaceutical preparation, in adhesiveness to the mucosa and in sustained action. ① It contains a polymer having good initial adhesiveness (hereinafter referred to as "initial adhesion polymer"); ② it contains a polymer having good shape retaining property (hereinafter referred to as "shape-retaining polymer"); ③ it contains a physiologically active substance; ④ it contains a liquid substance; ⑤ the initial adhesion polymer and shape-retaining polymer are dispersed in the liquid substance; ⑥ the physiologically active substance is dispersed or dissolved in the liquid substance; and ⑦ the total moisture content in the preparation as a whole is not more than 2%. The present invention has now been completed based on the above and other findings.

The invention is described below in further detail.

The phenomenon that when a water-soluble polymer is brought into contact with water, the surface thereof is dissolved and the polymer exhibits adhesiveness is generally and well known. In that case, when a system where the water-soluble polymer has been dissolved in the oil beforehand is compared with a system where said polymer is dispersed therein in the form of particles, a distinct difference in adhesiveness is observable, namely the system containing said polymer dispersed therein in the form of particles is superior in adhesiveness.

The present inventors made experiments concerning the above particular phenomenon and, as a result, found that, for increasing the adhesiveness, the adhesive polymer to be selected should, first of all, be dispersible in an oil in the form of fine particles and that, for attaining satisfactory adhesiveness and sustained action characteristics, two polymers differing in stickiness characteristics should be used combinedly.

A polymer which exhibits adhesiveness upon hydration, namely the initial adhesion polymer, is excellent in instantaneous adhesion but, since the rate of dissolution after gelation is rapid, the duration of adhesion is short. The shape-retaining polymer is contrary in characteristics; it retains the state of a high viscosity gel for a long period but is poor in instantaneous adhesion. Therefore, when either of these polymers is used singly, no satisfactory sustained action effect can be produced. On the contrary, when the initial adhesion polymer and shape-retaining polymer are uniformly blended beforehand in certain proportions and then dispersed, in the form of fine particles, in a liquid substance, good adhesion to the mucosa and excellent sustained release or action can be obtained.

The term "initial adhesion polymer" as used herein means a polymer or polymer capable of showing good adhesion characteristics in a short time. As typical examples thereof, there may be mentioned, among others, carboxyvinyl polymers and sodium polyacrylate. The term "shape-retaining polymer" means a compound capable of forming, upon hydration, a high viscosity gel erodible at a slow rate. Typical examples are cellulose derivatives (hydroxypropylcellulose, hydroxypropylmethylcellulose, etc.), among others.

The mixing ratio between the initial adhesion polymer and shape-retaining polymer (initial adhesion polymer::shape-retaining polymer) can be selected within the range of 1:9 to 9:1, preferably within the range of 2:8 to 8:2, depending on the sustained action period desired.

The pharmaceutical preparation or dosage form provided by the present invention (hereinafter referred to as "preparation of the invention") is a device obtained by dispersing the initial adhesion polymer and shape-retaining polymer (hereinafter sometimes collectively referred to as "adhesive polymers"), both in the form of solid particles, in a liquid substance and sufficiently maintaining the state of dispersion in liquid.

Therefore, the liquid substance to be used for the above purposes is required, first of all, to exhibit a liquid state at ordinary temperature. Since in the practice of the invention, the final dosage form is desirably a capsule form so that the liquid contents can be included therein in a simple and efficient manner, the liquid substance is also required to be incapable of inducing any physical or chemical change in the capsule or affecting the adhesive polymers.

As examples of the liquid substance that meet the above requirements, there may be mentioned liquid paraffin, vegetable oils, animal oils, and medium chain triglycerides, among others. The vegetable oils include soybean oil, peanut oil, cottonseed oil, sesame oil, etc. The animal oils include liver oil, egg yolk oil, fish oils, etc. These liquid substances may be used singly or two or more of them may be combinedly used. The mixing ratio between the adhesive polymers and liquid substance is suitably within the range of 1:0.5 to 1:20, preferably within the range of 1:1 to 1:9.

The moisture content in the preparation as a whole is limited to 2% or below so that the phenomenon of caking otherwise occurring in the capsules filled with the dispersion comprising the oil and water-soluble polymers can be prevented. The present inventors found that said caking phenomenon is caused by absorption, by the adhesive polymers, of small amounts of water occurring around the dispersion system, in particular in gelatin in the case of gelatin capsules, followed by dissolution of the surface of polymer particles and mutual binding of polymer particles. Based on such finding, the inventors succeeded in preventing the above-mentioned phenomenon of caking by drying the capsule to a total moisture content of not more than 2% and packaging the preparation with a packaging material excellent in moisture-proofness.

As mentioned above, when any one of the above requirements remains unsatisfied, any preparation showing good mucosa adhesion, release control and sustained action characteristics cannot be obtained.

For increasing the mucosa adhesion, it is desirable that the adhesive polymers be finer particles with a larger specific surface area. For rendering the adhesive polymer particles finer, a hammer mill, ball mill, or jet mill, for instance, may be used. The fine particles suitably have a mean particle size of not more than 100 μm, preferably not more than 50 μm.

For dispersing the adhesive polymers in the liquid substance, a stirrer, mixer, emulsifier or the like ordinary apparatus may simply be used. As such apparatus, a homogenizer, vacuum emulsifier, and colloid mill, for instance, may also be mentioned.

The physiologically active substance to which the present invention is to be applied may be one soluble in the liquid substance or one dispersible in the liquid substance. Such a physiologically active substance may be dissolved or dispersed in the liquid substance using an ordinary stirrer or mixer simultaneously with the procedure for dispersing the adhesive polymers in the liquid substance or after the step of dispersing the adhesive polymers in the liquid substance. The level of addition of the physiologically active substance may vary depending on the nature and/or properties thereof and other factors but, generally, it is suitably not more than 50% on the unit dose formulation basis.

As typical examples of the physiologically active substance, there may be mentioned the following compounds.

1. Antipyretic, analgesic and antiinflammatory agents

Indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrine, acetaminophen, benzydamine hydrochloride, phenylbutazone, flufenamic acid, mefenamic acid, sodium salicylate, choline salicylate, Sasapyrine (salsalate), clofezone, etodolac.

2. Antiulcer agents

Sulpiride, cetraxate hydrochloride, gefarnate, irsogladine maleate, cimetidine, ranitidine hydrochloride, famotidine, nizatidine, roxatidine acetate hydrochloride.

3. Coronary vasodilators

Nifedipine, isosorbide dinitrate, diltiazem hydrochloride, trapidil, dipyridamole, dilazep dihydrochloride, methyl 2,6-dimethyl- 4-(2-nitrophenyl)-5-(2-oxo-1,3,2-dioxaphosphorinan-2-yl)-1,4-dihydropyridine-3-carboxylate, verapamil, nicardipine, nicardipine hydrochloride, verapamil hydrochloride.

4. Peripheral vasodilators

Ifenprodil tartrate, cinepazide maleate, cyclandelate, cinnarizine, pentoxiphylline.

5. Antibiotics

Ampicillin, amoxicillin, cefalexin, erythromycin ethyl succinate, bacampicillin hydrochloride, minocycline hydrochloride, chloramphenicol, tetracycline, erythromycin.

6. Synthetic antimicrobial agents

Nalidixic acid, piromidic acid, pipemidic acid trihydrate, enoxacin, cinoxacin, ofloxacin, norfloxacin, ciprofloxacin hydrochloride, sulfamethoxazole-trimethoprim, 6-fluoro-1-methyl-7-[4-(5-methyl-2-oxo-1,3-dioxolen-4-yl)methyl-1-piperazinyl]-4-oxo- 4H[1,3]-thiazeto[3,2-a]quinoline-3-carboxylic acid.

7. Antispasmodic agents

Propantheline bromide, atropine sulfate, oxapium bromide, timepidium bromide, scopolamine butylbromide, trospium chloride, butropium bromide, N-methylscopolamine methylsulfate, octatropine methylbromide.

8. Antitussive and antiasthmatic agents

Theophylline, aminophylline, methylephedrine hydrochloride, procaterol hydrochloride, trimethoquinol hydrochloride, codeine phosphate, cromoglicate sodium, tranilast, dextromethorphan hydrobromide, dimemorfanphosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentanecitrate, oxeladin tannate, isoaminile citrate.

9. Bronchodilators

Diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide, methoxyphenamine hydrochloride.

10. Diuretic agents

Furosemide, acetazolamide, trichlormethiazide, cyclothiazide, hydrochlorothiazide, hydroflumethiazide, ethiazide, cyclopentiazide, spironolactone, triamterene, chlorothiazide, piretanide, mefruside, etacrynic acid, azosemide, clofenamide.

11. Muscle relaxants

Chlorphenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, dantrolene sodium.

12. Cerebral metabolism improving agents

Meclofenoxate hydrochloride.

13. Minor tranquilizers

Oxazolam, diazepam, clotiazepam, medazepam, temazepam, fludiazepam, meprobamate, nitrazepam, chlordiazepoxide.

14. Major tranquilizers

Sulpiride, clocapramine hydrochloride, zotepine, chloropromazine, haloperidol.

15. β-Blockers

Pindolol, propranolol hydrochloride, carteolol hydrochloride, metoprolol tartrate, labetalol hydrochloride, oxprenolol hydrochloride, acebutolol hydrochloride, bufetolol hydrochloride, alprenolol hydrochloride, arotinolol hydrochloride, nadolol, bucumolol hydrochloride, indenolol hydrochloride, timolol maleate, befunolol hydrochloride.

16. Antiarrhythmic agents

Procainamide hydrochloride, disopyramide, ajmaline, quinidine sulfate, aprindine hydrochloride, propafenone hydrochloride, mexiletine hydrochloride.

17. Antigout agents

Allopurinol, probenecid, colchicine, sulfinpyrazone, benzbromarone, bucolome.

18. Anticoagulants

Ticlopidine hydrochloride, dicoumarol, warfarin potassium.

19. Antiepileptics

Phenytoin, sodium valproate, metharbital, carbamazepine.

20. Antihistaminics

Chlorpheniramine maleate, clemastine fumarate, mequitazine, alimemazine tartrate, cyproheptadine hydrochloride.

21. Antiemetics

Difenidol hydrochloride, metoclopramide, domperidone, betahistine mesilate, trimebutine maleate.

22. Antihypertensive agents

Dimethylaminoethyl reserpilinate hydrochloride, rescinnamine, methyldopa, prazosin hydrochloride, bunazosin hydrochloride, clonidine hydrochloride, budralazine, urapidil.

23. Sympathomimetic agents

Dihydroergotamine mesilate, isoproterenol hydrochloride, etilefrine hydrochloride.

22. Expectorants

Bromhexine hydrochloride, carbocysteine, cysteineethyl ester hydrochloride, cysteine methyl ester hydrochloride.

25. Oral antidiabetic agents

Glibenclamide, tolbutamide, glymidine sodium.

26. Cardiovascular system drugs

Ubidecarenone, ATP 2Na.

27. Iron preparations

Ferrous sulfate, dried iron sulfate.

28. Vitamins

Vitamin $B_1$, vitamin $B_2$, vitamin $B_6$, vitamin $B_{12}$, vitamin C, folic acid.

29. Therapeutic agents for pollakiuria

Flavoxate hydrochloride, oxybutynin hydrochloride, terodiline hydrochloride, 4-diethylamino-1,1-dimethyl-2-butynyl (+)-α-cyclohexyl-α-phenylglycolate hydrochloride monohydrate.

30. Angiotensin converting enzyme inhibitors

Enalapril maleate, alacepril, delapril hydrochloride.

BEST MODES FOR CARRYING OUT THE INVENTION

The following examples, comparative examples and test examples illustrate the present invention in further detail.

EXAMPLE 1

To 999 g of liquid paraffin (1st reagent grade; Kanto Chemical Co.) weighed as a liquid substance, there were added 150 g of Hiviswako (trademark: Hiviswako 104; Wako Pure Chemical Industries) as an initial adhesion polymer, 174 g of hydroxypropylmethylcellulose (trademark: Metolose 60SH-4000; Shin-etsu Chemical Co.) and 177 g of hydroxypropylcellulose (type H; Nippon Soda Co.) as shape-retaining polymer, and 24 g of methyl 2,6-dimethyl-4-(2-nitrophenyl)-5-(2-oxo-1,3,2-dioxaphosphorinan-2-yl)- 1,4-dihydropyridine-3-carboxylate with a mean particle size of 60 μm as a physiologically active substance. The resultant mass was charged into a mixing agitator (vacuum decoction type, model 5PMV-r; San-ei Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each filled with a total weight of 508 mg of the dispersion and then sealed with a gelatin band. The liquid composition-filled capsules were then charged into a fluidized bed granulating and coating apparatus (STREA type 1; Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The moisture content in each capsule was 1.8%.

EXAMPLE 2

To 353 g of liquid paraffin (1st reagent grade; Kanto Chemical Co.) weighed as a liquid substance, there were added 44 g of Hiviswako (trademark: Hiviswako 104; Wako Pure Chemical Industries) as an initial adhesion polymer, 103 g of hydroxypropylmethylcellulose (trademark: Metolose 60SH-4000; Shin-etsu Chemical Co.) as a shape-retaining polymer, and 28 g of methyl 2,6-dimethyl-4-(2-nitrophenyl)- 5-(2-oxo-1,3,2-dioxaphosphorinan-2-yl)-1,4-dihydropyridine- 3-carboxylate with a mean particle size of 15 μm as a physiologically active substance. The resultant mass was charged into a mixing agitator (vacuum decoction type, model 5PMV-r; San-el Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each. filled with a total weight of 508 mg of the dispersion and then sealed with a gelatin band. The liquid composition-filled capsules were then charged into a fluidized bed granulating and coating apparatus (STREA type 1; Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The moisture content in each capsule was 1.7%.

EXAMPLE 3

To 377 g of soybean oil (Nakarai Tesque) weighed as a liquid substance, there were added 38 g of Hiviswako (trademark: Hiviswako 104; Wako Pure Chemical Industries) as an initial adhesion polymer, 88 g of hydroxypropylmethylcellulose (trademark: Metolose 90SH-6000; Shin-etsu Chemical Co.) as a shape-retaining polymer, and 5 g of oxybutynin hydrochloride (chemically, 4-dimethylamino-2-butynyl α-phenylcyclohexaneglycolate hydrochloride) with a mean particle size of 30 μm as a physiologically active substance. The resultant mass was charged into a mixing agitator (vacuum decoction type, model 5PMV-r; San-el Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each filled with a total weight of 508 mg of the dispersion and then sealed with a gelatin band. The liquid composition-filled capsules were then charged into a fluidized bed granulating and coating apparatus (STREA type Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The moisture content in each capsule was 1.7%.

EXAMPLE 2

To 333 g of liquid paraffin (1st reagent grade; Kanto Chemical Co.) weighed as a liquid substance, there were added 47 g of Hiviswako (trademark: Hiviswako 104; Wako Pure Chemical Industries) as an initial adhesion polymer, 55 g of hydroxypropylmethylcellulose (trademark: Metolose 60SH-4000; Shin-etsu Chemical Co.) and 55 g of hydroxypropylcellulose (type H; Nippon Soda Co.) as shape-retaining polymers, and 20 g of nifedipine (Yodogawa Pharmaceutical Co.) with a mean particle size of 20 μm as a physiologically active substance. The resultant mass was charged into a mixing agitator (vacuum decoction type, model 5PMV-r; San-ei Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each filled with a total weight of 510 mg of the dispersion and then sealed with a gelatin band. The liquid composition-filled capsules were then charged into a fluidized bed granulating and coating apparatus (STREA type 1; Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The moisture content in each capsule was 1.6%.

EXAMPLE 5

To 333 g of medium chain triglyceride (trademark: Panacete 810; Nippon Oils and Fats Co.) weighed as a liquid substance, there were added 47 g of Hiviswako (trademark: Hiviswako 104; Wako Pure Chemical Industries) as an initial adhesion polymer, 55 g of hydroxypropylmethylcellulose (trademark: Metolose 60SH- 4000; Shin-etsu Chemical Co.) and 55 g of hydroxypropylcellulose (type H;

Nippon Soda Co.) as shape-retaining polymers, and 20 g of nicardipine hydrochloride with a mean particle size of 16 μm as a physiologically active substance. The resultant mass was charged into a mixing agitator (vacuum decoction type, model 5PMV-r; San-ei Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each filled with a total weight of 510 mg of the dispersion and then sealed with a gelatin band. The liquid composition-filled capsules were then charged into a fluidized bed granulating and coating apparatus (STREA type 1; Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The capsules thus obtained were named formulation a capsules.

Further, capsules, named formulation b capsules, were prepared from 382 g of the medium chain triglyceride mentioned above, 30 g of Hiviswako, 39 g of hydroxypropylmethylcellulose, 39 g of hydroxypropylcellulose and 20 g of nicardipine hydrochloride in the same manner as mentioned above.

Still further, capsules, named formulation c capsules, were prepared from 437 g of the medium chain triglyceride, 15 g of Hiviswako, 19 g of hydroxypropylmethylcellulose, 19 g of hydroxypropylcellulose and 20 g of nicardipine hydrochloride.

The moisture contents per capsule were 1.7%, 1.5% and 1.6%, respectively.

The formulation a, b and c capsules were used as samples for a dissolution test.

EXAMPLE 6

To 357 g of soybean oil (Nakarai Tesque) weighed as a liquid substance, there were added 43 g of sodium polyacrylate (Nakarai Tesque) as an initial adhesion polymer, 100 g of hydroxypropylcellulose (type H; Nippon Soda Co.) as a shape-retaining polymer, and 15 g of nicorandil with a mean particle size of 25 μm as a physiologically active substance. The resultant mass was charged into a mixing agitator (vacuum decoction type, model 5PMV-r; San-ei Seisakusho) and mixing and dispersion were effected under suction by means of a vacuum pump at a vessel inside temperature of 50° C. for 1 hour to give a uniform dispersion with a moisture content of not more than 1%.

Hard capsules of size #0 were each filled with a total weight of 515 mg of the dispersion and then sealed with a gelatin band. The liquid composition-filled capsules were then charged into a fluidized bed granulating and coating apparatus (STREA type 1; Powrex Co.), where the capsules were preheated and dried at a supplied air temperature of 50° C. for about 20 minutes and then sprayed with a 5% (w/v) solution of hydroxypropylcellulose (type SL; Nippon Soda Co.) in ethanol. Each capsule was thus provided with 30 mg of a coat film. The capsules thus obtained were named formulation d capsules.

Further, capsules, named formulation e capsules, were prepared from 390 g of soybean oil, 33 g of sodium polyacrylate, 42 g of hydroxypropylcellulose and 15 g of nicorandil in the same manner as mentioned above.

Still further, capsules, named formulation f capsules, were prepared from 440 g of soybean oil, 18 g of sodium polyacrylate, 42 g of hydroxypropylcellulose and 15 g of nicorandil in the same manner as mentioned above. The moisture contents per capsule were 1.6%, 1.8% and 1.8%, respectively.

The formulation d, e and f capsules were used as samples for a dissolution test.

Comparative Example 1

Preparation of an Undried Test Sample

To 333 g of liquid paraffin (1st reagent grade; Kanto Chemical Co.) weighed as a liquid substance, there were added 50 g of Hiviswako (trademark: Hiviswako 104; Wako Pure Chemical Industries) as an initial adhesion polymer, 58 g of hydroxypropylmethylcellulose (trademark: Metolose 60SH-4000; Shin-etsu Chemical Co.) and 177 g of hydroxypropylcellulose (type H; Nippon Soda Co.) as shape-retaining polymers, and 8 g of methyl 2,6-dimethyl-4-(2-nitrophenyl)- 5-(2-oxo-1,3,2-dioxaphosphorinan-2-yl)-1,4-dihydropyridine- 3-carboxylate with a mean particle size of 60 μm as a physiologically active substance. The resultant mass was charged into a mixing agitator (vacuum decoction type, model 5PMV-r; San-ei Seisakusho) and mixing and dispersion were effected at ordinary temperature (25° C.) and ordinary pressure for 1 hour to give a uniform dispersion.

Hard capsules of size #0 were each filled with a total weight of 508 mg of the dispersion and then sealed with a gelatin band. The liquid composition-filled capsules were then charged into a fluidized bed granulating and coating apparatus (STREA type 1; Powrex Co.), where the capsules were sprayed with a 5% (w/v) solution of hydroxypropylcellulose (type SL; Nippon Soda Co.) in ethanol. Each capsule was thus provided with 30 mg of a coat film. The moisture content in each capsule was 3.1%.

Comparative Example 2

Hydroxypropylcellulose 70 g (type L; Nippon Soda Co.) was dissolved in purified water to give a 5% (w/v) aqueous solution. The solution was sprayed onto 1,000 g of nonpareil (trademark: Nonpareil 103; particle size 350–500 μm; Freund Industrial Co.) charged into a centrifugal fluidized bed granulator (model CF-360; Freund Industrial Co.) while gradually spraying a uniform powder mixture composed of 80 g of methyl 2,6-dimethyl-4-(2-nitrophenyl)-5-(2-oxo-1, 3,2-dioxaphosphorinan-2-yl)-1,4-dihydropyridine-3-carboxylate and 850 g of corn starch, to give spherical granules.

The granules were then dried using a fluidized bed drier to give granules with a main ingredient content of 99.8%. Then, 500 g of the granules were charged into a centrifugal fluidized bed granulator (model CF-360; Freund Industrial Co.) and sprayed with a total of 250 g of a dispersion of 60 g of an aminoalkyl methacrylate polymer (trademark: Eudragit RS; Rohm Pharma), 2.5 g of triethyl citrate (trademark: Citroflex 2; Pfizer) and 7.5 g of talc in 157 g of purified water. About 530 g of coated granules were obtained and used as a preparation for comparison.

Test Example 1

Ten capsules each of the preparations of the invention obtained in Examples 1, 2 and 3 were tightly packed in bags (40 μm thick, 4×6 cm in size) made of an aluminum foil-laminated film having good moisture-proofness and, after tight closure, allowed to stand in a constant-temperature chamber maintained at 40° C. for 90 days. The capsules were then taken out and the capsule contents were observed. No change was noted.

Similarly, 10 comparative capsules of Comparative Example 1 were packed in a bag (40 μm thick, a 4×6 cm in size) made of an aluminum foil-laminated film having good moisture-proofness and, after tight closure, allowed to stand in a constant-temperature chamber maintained at 40° C. for 3 days. The capsules were then taken out and the capsule contents were observed. Caking had occurred and the contents were found wholly solidified.

Test Example 2

The test samples prepared in Examples 1 and 2 and Comparative Example 2 were respectively administered, together with 30 ml of water, to beagle dogs (3 per group, male, 8–12 kg) fasted overnight. Blood was sampled at timed intervals and the plasma concentration was determined by high performance liquid chromatography (HPLC).

As shown in FIG. 1, the test samples of Example 1 and 2 showed good sustained action characteristics as compared with the samples of Comparative Example 2.

Test Example 3

The test samples prepared in Example 1 and Comparative Example 1 and processed under severe conditions (namely the samples used in Test Example 1) were administered, together with 30 ml of water, to beagle dogs (3 per group, male, 8–12 kg) fasted overnight. Blood was sampled at timed intervals and the plasma concentration was determined by high performance liquid chromatography (HPLC).

As shown in FIG. 2, the samples of Example 1 showed good absorption and sustained action characteristics. On the contrary, the test samples of Comparative Example 1 in which caking had occurred as a result of storage at 40° C. gave, at every point of assay, only a slight detectable plasma level of methyl 2,6-dimethyl- 4-(2-nitrophenyl)-5-(2-oxo-1, 3,2-dioxaphosphorinan-2-yl)- 1,4-dihydropyridine-3-carboxylate.

Test Example 4

Data on Adhesiveness; Peeling Method

A dispersion of 1 part of Hiviswako or hydroxypropylcellulose in 2 parts of soybean oil (Test sample 2 or 3, respectively), a solution (2%, w/v) of Hiviswako or hydroxypropylcellulose in purified water (Test sample 4 or 5, respectively), a solution (2%, w/v) of hydroxypropylcellulose in propylene glycol (Test sample 6) and a solution (2%, w/v) of Hiviswako in polyethylene glycol 400 (PEG-400) (Test sample 7) were prepared.

On a 3.14 cm² Teflon film was placed 500 mg of each test sample, which was then superficially hydrated with the first fluid prescribed in the Japanese Pharmacopeia (pH 1.2) for 60 seconds. The sample was transferred to a phenol resin plate in accordance with the Japanese Pharmacopeia adhesive strength test method for adhesive plasters. The test sample was then scraped off by means of a Delrin scraper having a weight of 150 g and an edge angle of 60° at a rate of pulling of 300 mm/min and a distance of 20 mm using a material testing machine (Autograph AG-5000, Shimadzu) fitted with a 5 kg load cell, and the peel force was measured for comparison with regard to adhesiveness.

TABLE 1

| Test sample | Maximum peel force (g/cm²) |
| --- | --- |
| (1) Soybean oil alone | 0 |
| (2) Hiviswako dispersed in soybean oil | 320 |
| (3) HPC-H dispersed in soybean oil | 340 |
| (4) Hiviswako dissolved in purified water | 5 |
| (5) HPC-H dissolved in purified water | 7 |
| (6) HPC-H dissolved in PG | 4 |
| (7) Hiviswako dissolved in PEG-400 | 4 |

HPC-H: Hydorxypropylcellulose type H
PG: Propylene glycol
PEG-400: Polyethylene glycol 400

As shown in Table 1, Test samples 4, 5, 6 and 7, which contained both the initial adhesion polymer (Hiviswako) and shape-retaining polymer (HPC-H) in dissolved form, showed little adhesiveness. On the other hand, Test samples 2 and 3, which contained one of the polymers mentioned above in the form of a dispersion of particles, showed strong adhesiveness.

TABLE 2

| | Test sample No. | | | |
| --- | --- | --- | --- | --- |
| | 1 | 2 | 3 | 4 |
| Blue No. 1 lake | 10 | 10 | 10 | 10 |
| Hiviswako | 100 | | | 50 |
| HPC-H | | 100 | | 50 |
| PVP | | | 100 | |
| Liquid paraffin | 200 | 200 | 200 | 200 |
| | | | | (in mg) |

HPC-H: Hydroxypropylcellulose type H
PVP: Polyvinylpyrrolidone

The above test samples were respectively administered to rats (5 per group) at a dose of 100 μl. At 1, 3, 5, 7 and 10 hours after administration, the animals were laparotomized and observed for the transfer of each preparation in the gastrointestinal tract.

TABLE 3

| | Time (hours) | | | | |
| --- | --- | --- | --- | --- | --- |
| Test sample No. | 1 | 3 | 5 | 7 | 10 |
| 1 | ⊙ | Δ | X | X | |
| 2 | ⊙ | O | Δ | X | |
| 3 | Δ | X | X | | |
| 4 | ⊙ | ⊙ | O | Δ | X |

⊙: Mostly retained in the stomach.
O: Considerable retention in the stomach, with partial migration into the small intestine.
Δ: Mostly found in the small intestine, with slight retention in the stomach.
X: No retention in the stomach; mostly dissolved or eliminated.

As shown in Table 3, Test sample No. 4, which contained an equal weight mixture of Hiviswako as an initial adhesion polymer and hydroxypropylcellulose (H type) as a shape-retaining polymer in the form of a dispersion in liquid paraffin, showed excellent adhesiveness and the rate of transfer thereof to the small instestine could successfully retarded, as compared with the samples containing only one single polymer.

Test Example 5

The capsule prepared in Example 4 (nifedipine content: 20 mg) or a commercial rapid dissolution nifedipine capsule (trademark: Anpect; nifedipine content: 10 mg; Nippon Shinyaku) was administered, together with 30 ml of water, to each of 3 beagle dogs (male, 8–12 kg) fasted overnight at a dose of 1 capsule per animal. Blood was sampled at timed intervals and the plasma nifedipine level was determined by high performance liquid chromatography (HPLC).

The results thus obtained revealed, as shown in FIG. 3, markedly prolonged action of the sample of Example 4 as compared with the commercial rapid dissolution capsule.

Test Example 6

The capsule prepared in Example 3 (oxybutynin hydrochloride content: 5 mg) and a commercial oxybutynin hydrochloride tablet (trademark: Pollakisu tablet; oxybutynin hydrochloride content: 3 mg/Kodama) were tested for dissolution by the paddle method (200 rpm) using 1,000 ml of the first fluid for disintegration test as prescribed in the Japanese Pharmacopeia (12th edition). The test fluids were sampled at timed intervals and assayed for oxybutynin hydrochloride by high performance liquid chromatography.

The results thus obtained revealed, as shown in FIG. 4, that the capsule prepared in Example 3 showed, in the test fluid, a dissolution behavior clearly suggestive of its characteristics as a sustained release preparation.

Test Example 7

The capsules prepared in Example 5 (formulations a, b and c; nicardipine hydrochloride content: 20 mg) and a commercial nicardipine hydrochloride tablet (trademark: Perdipine; nicardipine hydrochloride content: 10 mg; Yamanouchi Pharmaceutical) were subjected to dissolution test in the same manner as in Test Example 6.

The results thus obained revealed, as shown in FIG. 5, that the capsules prepared in Example 5 showed, in the test fluid, a dissolution behavior clearly suggestive of their charcterisitcs as a sustained release preparation. It is further evident that the dissolution behavior could be controlled as desired by making changes in the composition of capsule contents and the levels of addition.

Test Example 8

The capsules prepared in Example 6 (nicorandil content: 15 mg; capsule formulations d, e and f) and a commercial nicroandil tablet (trademark: Sigmart; nicorandil content: 5 mg; Chugai Pharmaceutical) were subjected to dissolution test in the same manner as in Test Example 6.

The results thus obtained revealed, as shown in FIG. 6, that the capsules prepared in Example 6 showed, in the test fluid, a dissolution behavior clearly suggestive of their characteristics as a sustained release preparation. It is further evident that the dissolution behavior could be controlled as desired by making changes in the composition of capsule contents and the levels of addition.

The time (hours) is on the abscissa and the plasma level (ng/ml) of methyl 2,6-dimethyl-4-(2-nitrophenyl)-5-(2-oxo-1,3,2-dioxaphosphorinan- 2-yl)-1,4-dihydropyridine-3-carboxylate on the ordinate.

The symbol $\triangle$ indicates the plasma level of the preparation of the invention prepared in Example 1, ● of the preparation of the invention prepared in Example 2, and ▫ of the preparation prepared in Comparative Example 2.

Figure 1:
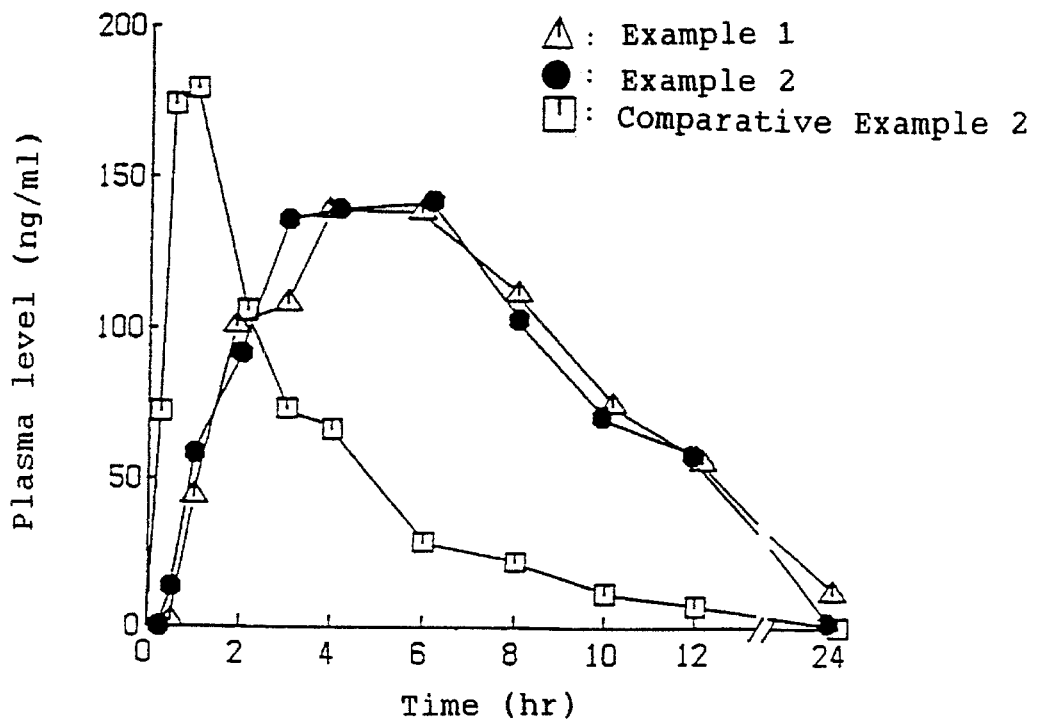
FIG. 1 graphically shows the time courses of the plasma level of methyl 2,6-dimethyl-4-(2-nitrophenyl)-5-(2-oxo-1, 3,2-dioxaphosphorinan- 2-yl)-1,4-dihydropyridine-3-carboxylate following oral administration of the preparations of the invention as prepared in Example 1 and Example 2 and the preparation prepared in Comparative Example 2 to beagle dogs (3 per group).
Figure 2:
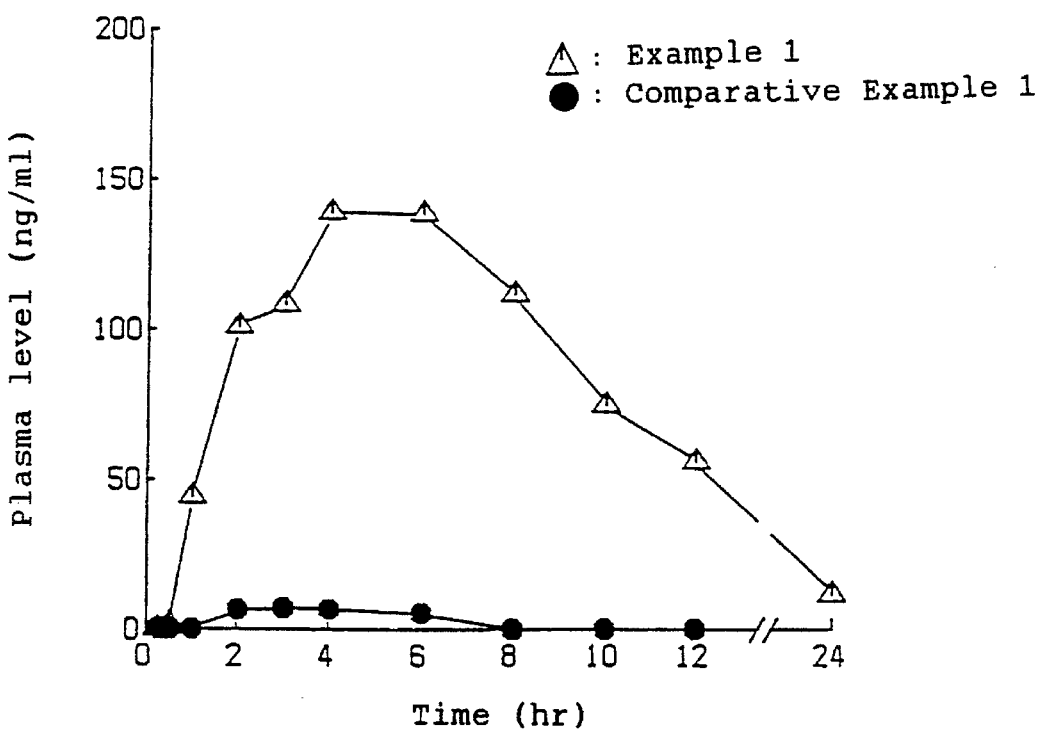

FIG. 2 graphically shows the time courses of the plasma level of methyl 2,6-dimethyl-4-(2-nitrophenyl)-5-(2-oxo-1, 3,2-dioxaphosphorinan- 2-yl)-1,4-dihydropyridine-3-carboxylate following oral administration of the preparation of the invention prepared in Example 1 and the preparation prepared in Comparative Example 1 to beagle dogs (3 per group).

The time (hours) is on the abscissa and the plasma level (ng/ml) of methyl 2,6-dimethyl-4-(2-nitrophenyl)-5-(2-oxo-1,3,2-dioxaphosphorinan- 2-yl)-1,4-dihydropyridine-3-carboxylate on the ordinate.

The symbol $\triangle$ indicates the plasma level of the preparation of the invention prepared in Example 1, and ● of the preparation prepared in Comparative Example 1.

Figure 3:
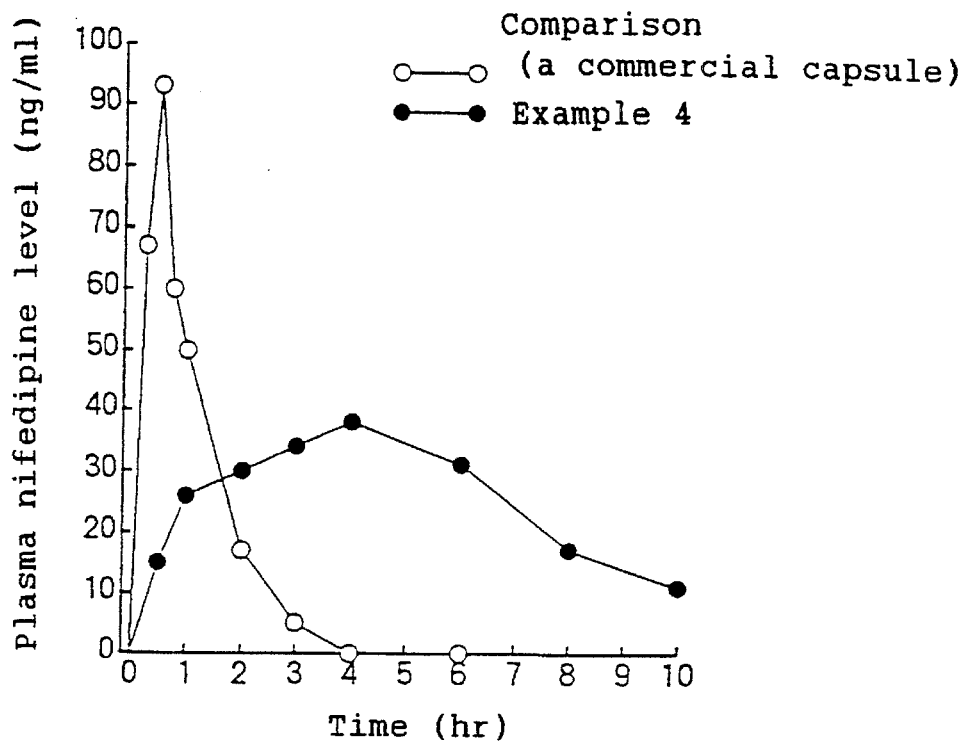

FIG. 3 shows the time courses of the plasma nifidipine level following oral administration of the preparation of the invention prepared in Example 4 and a commercial capsule to beagle dogs.

The time (hours) is on the abscisss and the plasma nifedipine level (ng/ml) on the ordinate. The symbol ● indicates the preparation of the invention prepared in Example 4, and ○ the commercial capsule.

Figure 4:
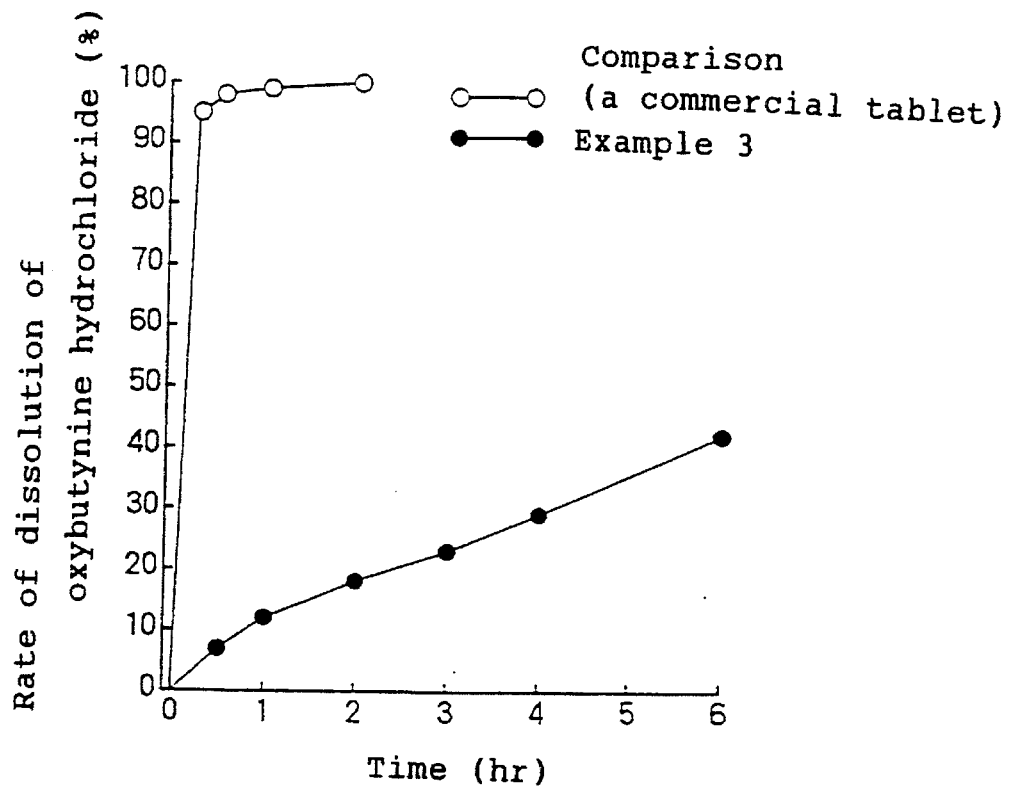

FIG. 4 shows the dissolution behaviors in the first fluid of the Japanese Pharmacopeia of the preparation of the invention prepared in Example 3 and a commercial tablet.

The time (hours) is on the abscissa and the rate (%) of dissolution of oxybutynine hydrochloride on the ordinate. The symbol ● indicates the preparation of the invention prepared in Example 3 and ○ the commercial tablet.

Figure 5:
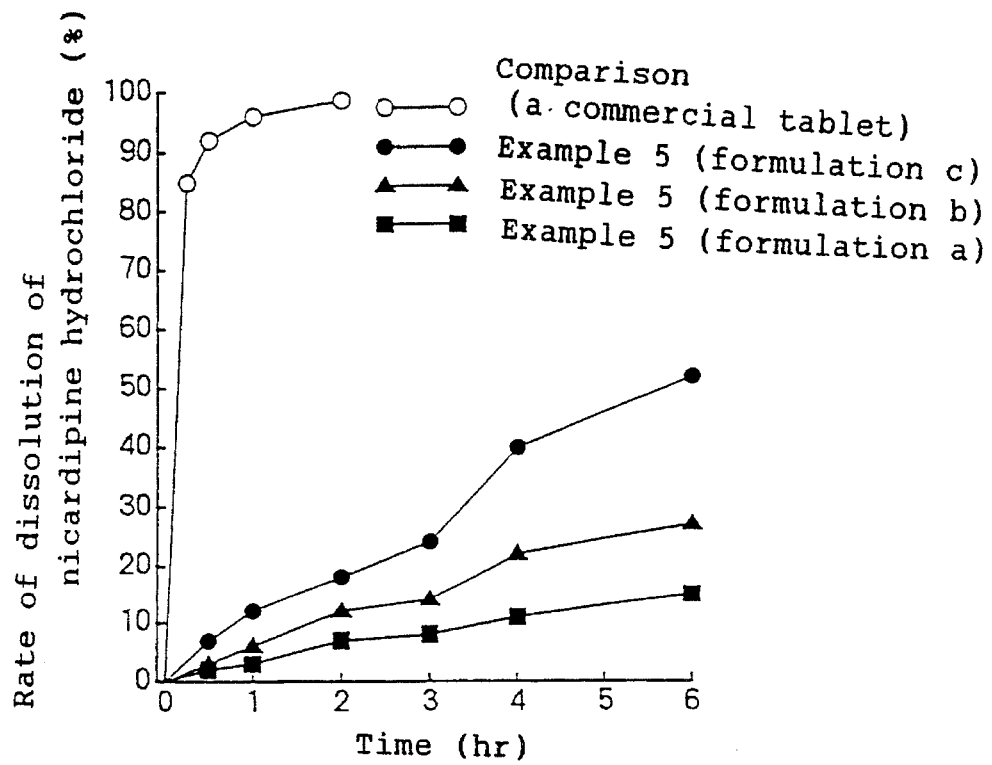

FIG. 5 shows the dissolution behaviors in the first fluid of the Japanese Pharmacopeia of the preparation of the invention prepared in Example 5 and a commercial tablet.

The time (hours) is on the abscissa and the rate (%) of dissolution of nicardipine hydrochloride on the ordinate. The symbols ■, ▲ and ● indicate the formulation a, b and c capsules, respectively, as prepared in Example 5 while increasing the level of addition of the medium chain triglyceride in the preparation of the invention, and ○ indicates the commercial tablet.

Figure 6:
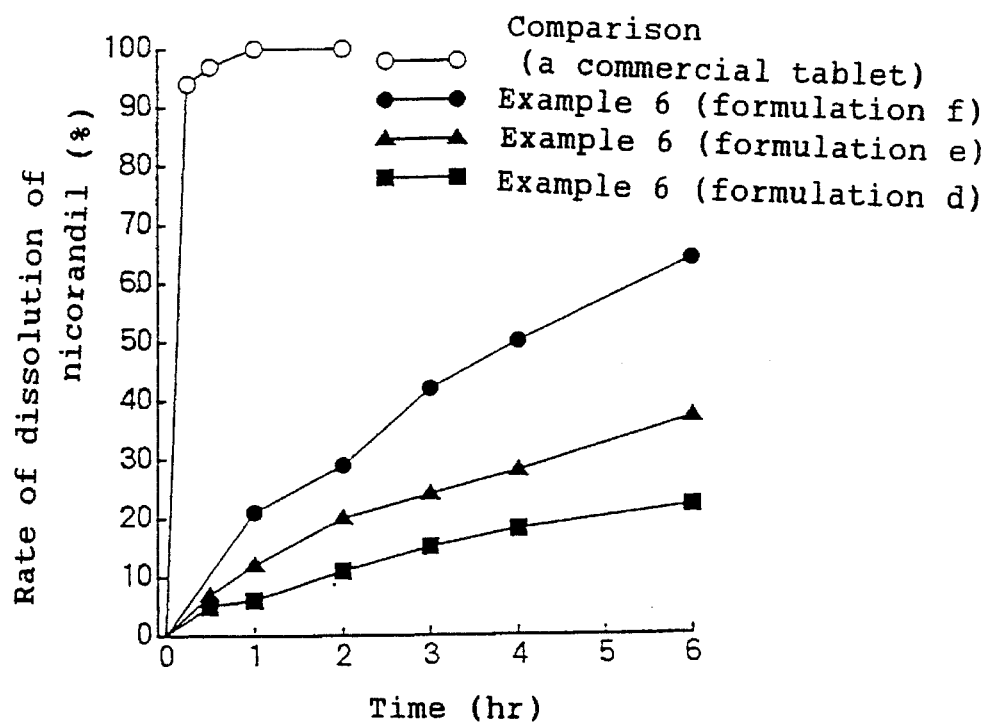

FIG. 6 shows the dissolution behaviors in the first fluid of the Japanese Pharmacopeia of the preparation of the invention prepared in Example 6 and a commercial tablet.

The time (hours) is on the abscissa and the rate (%) of dissolution of nicorandil on the ordinate. The symbols ■, ▲ and ● indicate the formulation d, e and f capsules, respectively, as prepared in Example 6 while increasing the level of addition of soybean oil in the preparation of the invention, and ○ indicates the commercial tablet.

We claim:

1. A capsule which contains a sustained release preparation in the form of a dispersion comprising:
    (a) a first water soluble polymer, selected from the group consisting of carboxyvinyl polymers and sodium polyacrylate that is capable of dispersing in a liquid substance selected from the group consisting of lipids, fats and oils in the form of solid particles and showing instantaneous adhesion upon hydration;

(b) a second water-soluble polymer that is capable of dispersing in a liquid substance selected from the group consisting of lipids, fats and oils in the form of solid particles, and is capable of showing instantaneous adhesion upon hydration but retains the state of gel;

(c) a physiologically active substance; and (d) a liquid substance selected from the group consisting of lipids, fats and oils;

wherein the first polymer and the second polymer are dispersed in said liquid substance, the first polymer and the second polymer are in the ratio of 1:9 to 9:1, the physiologically active substance is dispersed or dissolved in the liquid substance, and the total water content in the preparation is not more than 2%.

2. A method for control of drug concentration in blood in animals and humans, which comprises administering to an animal or human in need thereof a capsule according to claim 1.

3. A capsule according to claim 1 wherein said first polymer is a carboxyvinyl polymer.

4. A capsule according to claim 1 wherein said second water-soluble polymer is a cellulose ether.

5. A capsule according to claim 4 wherein said cellulose ether is hydroxypropylcellulose or hydroxypropylmethylcellulose.

6. The method according to claim 2 wherein said liquid substance is selected from one or more of the group consisting of liquid paraffin, vegetable oils, animal oils and medium chain triglycerides.

7. A capsule according to claim 1 wherein the ratio of the first polymer and the second polymer is within the range of 2:8 to 8:2.

8. The method according to claim 6 wherein said vegetable oil is soybean oil, peanut oil, cottonseed oil or sesame oil.

9. A capsule according to claim 1 wherein said liquid substance is selected from one or more of the group consisting of liquid paraffin, vegetable oils, animal oils and medium chain triglycerides.

10. A capsule according to claim 9 wherein said vegetable oil is soybean oil, peanut oil, cottonseed oil or sesame oil.

11. A capsule according to claim 9 wherein said animal oil is liver oil, egg yolk oil or fish oil.

12. A capsule according to claim 1 wherein the first and second polymers together are in a mixing ratio with the liquid substance within a range of 1:0.5 to 1:20.

13. A capsule according to claim 12 wherein said mixing ratio is within the range of 1:1 to 1:9.

14. A capsule according to claim 1 wherein said physiologically active substance is selected from the group consisting of antipyretic agents, analgesic agents, anti-inflammatory agents, antiulcer agents, coronary vasodilators, peripheral vasodilators, antibiotics, synthetic antimicrobial agents, antispasmodic agents, antitussive agents, antiasthmatic agents, bronchodilators, diuretic agents, muscle relaxants, cerebral metabolism improving agents, minor tranquilizers, major tranquilizers, β-blockers, antiarrhythmic agents, antigout agents, anticoagulants, antiepileptics, antihistaminics, antiemetics, antihypertensive agents, sympathomimetic agents, expectorants, oral antidiabetic agents, cardiovascular system drugs, iron preparations, vitamins, therapeutic agents for pollakiuria, and angiotensin-converting enzyme inhibitors.

15. The method according to claim 6 wherein said animal oil is liver oil, egg yolk oil or fish oil.

16. The method according to claim 2 wherein said first polymer is a carboxyvinyl polymer.

17. The method according to claim 2 wherein said second water-soluble polymer is a cellulose ether.

18. A capsule according to claim 17 wherein said cellulose ether is hydroxypropylcellulose or hydroxypropylmethylcellulose.

19. The method according to claim 2 wherein the first and second polymers together are in a mixing ratio with the liquid substance within a range of 1:0.5 to 1:20.

20. A method according to claim 2 wherein the ratio of the first polymer and the second polymer is within the range of 2:8 to 8:2.

21. The method according to claim 19 wherein said mixing ratio is within the range of 1:1 to 1:9.

22. The method according to claim 2 wherein said physiologically active substance is selected from the group consisting of antipyretic agents, analgesic agents, anti-inflammatory agents, antiulcer agents, coronary vasodilators, peripheral vasodilators, antibiotics, synthetic antimicrobial agents, antispasmodic agents, antitussive agents, antiasthmatic agents, bronchodilators, diuretic agents, muscle relaxants, cerebral metabolism improving agents, minor tranquilizers, major tranquilizers, β-blockers, antiarrhythmic agents, antigout agents, anticoagulants, antiepileptics, antihistaminics, antiemetics, antihypertensive agents, sympathomimetic agents, expectorants, oral antidiabetic agents, cardiovascular system drugs, iron preparations, vitamins, therapeutic agents for pollakiuria, and angiotensin-converting enzyme inhibitors.

\* \* \* \* \*